(12) United States Patent
Flaschenriem

(10) Patent No.: US 11,559,016 B2
(45) Date of Patent: Jan. 24, 2023

(54) *CATHARANTHUS* HYBRID 'PAS1305707' AND PARENT THEREOF

(71) Applicant: Ball Horticultural Company, West Chicago, IL (US)

(72) Inventor: Denis R. Flaschenriem, Savage, MN (US)

(73) Assignee: Ball Horticultural Company, West Chicago, IL (US)

( * ) Notice: Subject to any disclaimer, the term of this patent is extended or adjusted under 35 U.S.C. 154(b) by 151 days.

(21) Appl. No.: 17/011,441

(22) Filed: Sep. 3, 2020

(65) Prior Publication Data

US 2022/0061245 A1 Mar. 3, 2022

(51) Int. Cl.
*A01H 6/08* (2018.01)
*A01H 5/02* (2018.01)

(52) U.S. Cl.
CPC .............. *A01H 6/084* (2018.05); *A01H 5/02* (2013.01)

(58) Field of Classification Search
CPC .................................................... A01H 6/084
See application file for complete search history.

(56) References Cited

U.S. PATENT DOCUMENTS 9,451,748 B2 * 9/2016 Flaschenriem ........ A01H 6/084
9,451,752 B2 9/2016 Flaschenriem

OTHER PUBLICATIONS

Plant Resources of Tropical Africa 11(1) Medicinal Plants 1, ed. G.H. Schmelzer and A. Gurib-Fakim, PROTA Foundation, Wageningen, Netherlands, pp. 152-159, 2008.
Variety specific information as indicated in transmittal letter of Information Disclosure Statement for U.S. Appl. No. 17/011,441, filed Nov. 13, 2020.

* cited by examiner

*Primary Examiner* — David H Kruse
(74) *Attorney, Agent, or Firm* — Dentons US LLP

(57) ABSTRACT

The invention provides seeds and plants of *Catharanthus* hybrid 'PAS1305707' and the parent lines thereof. The invention thus relates to the plants, seeds, plant parts, and tissue cultures of *Catharanthus* hybrid 'PAS1305707' and the parent lines thereof, and to methods for producing a *Catharanthus* plant produced by crossing such plants with themselves or with another *Catharanthus* plant, such as a plant of another genotype. The invention further relates to seeds and plants produced by such crossing. The invention further relates plants, seeds, plant parts and tissue cultures of *Catharanthus* hybrid 'PAS1305707' and the parent lines thereof comprising introduced beneficial or desirable traits.

28 Claims, No Drawings

*CATHARANTHUS* HYBRID 'PAS1305707' AND PARENT THEREOF

FIELD OF THE INVENTION

The present invention relates to the field of plant breeding and, more specifically, to the development of *Catharanthus* hybrid 'PAS1305707' and the parent *Catharanthus* line R2358D.

BACKGROUND OF THE INVENTION

Of the eight known *Catharanthus* species, seven originate from Madagascar, and the exception *Catharanthus pusillus* is endemic to India and Sri Lanka. Of importance is *Catharanthus roseus*, commonly known as Madagascar periwinkle or vinca, which is valued for production of medicinal indole alkaloids. In addition, it is frequently grown annually from seed or less commonly cuttings in temperate climates for use in summer bedding or as a pot plant. It has long been grown as an ornamental in tropical regions of the world. As a consequence of its ability to self-pollinate, *Catharanthus roseus* is now widely naturalized in many tropical regions. Hybridization is less common; however, there are natural hybrids between *Catharanthus longifolius* and *Catharanthus roseus*. Man-made crosses have yielded hybrids between *Catharanthus ovalis* and *Catharanthus longifolius*, and between *Catharanthus roseus* and *Catharanthus trichophyllus*.

SUMMARY OF THE INVENTION

In one aspect, the present invention provides a *Catharanthus* plant of the hybrid designated 'PAS1305707' or *Catharanthus* line R2358D. Also provided are *Catharanthus* plants having all the physiological and morphological characteristics of such a plant. Parts of these *Catharanthus* plants are also provided, for example, including a flower, pollen, a leaf, an ovule, an embryo, a seed, and a cell of the plant.

In another aspect of the invention, a plant of *Catharanthus* hybrid 'PAS1305707' or *Catharanthus* line R2358D comprising an added heritable trait is provided. The heritable trait may comprise a genetic locus that is, for example, a dominant or recessive allele. In one embodiment of the invention, a plant of *Catharanthus* hybrid 'PAS1305707' or *Catharanthus* line R2358D is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan.

The invention also concerns the seed of *Catharanthus* hybrid 'PAS1305707' or *Catharanthus* line R2358D. The *Catharanthus* seed of the invention may be provided, in particular embodiments, as an essentially homogeneous population of *Catharanthus* seed of *Catharanthus* hybrid 'PAS1305707' or *Catharanthus* line R2358D. Essentially homogeneous populations of seed are generally free from substantial numbers of other seed. Therefore, seed of hybrid 'PAS1305707' or *Catharanthus* line R2358D may be defined as forming at least about 90% of the total seed, including at least about 91%, 92%, 93%, 94%, 95%, 96%, 97%, 98%, 99%, or more of the seed. The seed population may be separately grown to provide an essentially homogeneous population of *Catharanthus* plants designated 'PAS1305707' or R2358D.

In yet another aspect of the invention, a tissue culture of regenerable cells of a *Catharanthus* plant of hybrid 'PAS1305707' or *Catharanthus* line R2358D is provided. The tissue culture will preferably be capable of regenerating *Catharanthus* plants capable of expressing all of the physiological and morphological characteristics of the starting plant, and of regenerating plants having substantially the same genotype as the starting plant. Examples of some of the physiological and morphological characteristics of the *Catharanthus* hybrid 'PAS1305707' and *Catharanthus* line R2358D include those traits set forth in the tables herein. The regenerable cells in such tissue cultures may be derived, for example, from embryos, meristems, cotyledons, pollen, leaves, anthers, roots, root tips, pistils, flowers, cuttings, seeds, and stems. Still further, the present invention provides *Catharanthus* plants regenerated from a tissue culture of the invention, the plants having all the physiological and morphological characteristics of *Catharanthus* hybrid 'PAS1305707' or *Catharanthus* line R2358D.

In still yet another aspect of the invention, processes are provided for producing *Catharanthus* seeds, plants and parts thereof, which processes generally comprise crossing a first parent *Catharanthus* plant with a second parent *Catharanthus* plant, wherein at least one of the first or second parent *Catharanthus* plants is a plant of *Catharanthus* line R2358D. These processes may be further exemplified as processes for preparing hybrid *Catharanthus* seed or plants, wherein a first *Catharanthus* plant is crossed with a second *Catharanthus* plant of a different, distinct genotype to provide a hybrid that has, as one of its parents, a plant of *Catharanthus* line R2358D. In these processes, crossing will result in the production of seed. The seed production occurs regardless of whether the seed is collected or not.

In one embodiment of the invention, the first step in "crossing" comprises planting seeds of a first and second parent *Catharanthus* plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent *Catharanthus* plants into plants that bear flowers. A third step may comprise preventing self-pollination of the plants, such as by emasculating the flowers (i.e., killing or removing the pollen).

A fourth step for a hybrid cross may comprise cross-pollination between the first and second parent *Catharanthus* plants. Yet another step comprises harvesting the seeds from at least one of the parent *Catharanthus* plants. The harvested seed can be grown to produce a *Catharanthus* plant or hybrid *Catharanthus* plant.

The present invention also provides the *Catharanthus* seeds and plants produced by a process that comprises crossing a first parent *Catharanthus* plant with a second parent *Catharanthus* plant, wherein at least one of the first or second parent *Catharanthus* plants is a plant of *Catharanthus* hybrid 'PAS1305707' or *Catharanthus* line R2358D. In one embodiment of the invention, *Catharanthus* seed and plants produced by the process are first generation (F1) hybrid *Catharanthus* seed and plants produced by crossing a plant in accordance with the invention with another, distinct plant. The present invention further contemplates plant parts of such an F1 hybrid *Catharanthus* plant, and methods of use thereof. Therefore, certain exemplary embodiments of the invention provide an F1 hybrid *Catharanthus* plant and seed thereof.

In still yet another aspect, the present invention provides a method of producing a plant derived from *Catharanthus* hybrid 'PAS1305707' or *Catharanthus* line R2358D, the method comprising the steps of: (a) preparing a progeny plant derived from *Catharanthus* hybrid 'PAS1305707' or *Catharanthus* line R2358D, wherein said preparing comprises crossing a plant of the hybrid 'PAS1305707' or *Catharanthus* line R2358D with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid 'PAS1305707' or *Catharanthus* line R2358D. The plant derived from hybrid 'PAS1305707' or line R2358D may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from *Catharanthus* hybrid 'PAS1305707' or *Catharanthus* line R2358D is obtained which possesses some of the desirable traits of the line/hybrid as well as potentially other selected traits.

In still yet another aspect of the invention, the genetic complement of *Catharanthus* hybrid 'PAS1305707' or *Catharanthus* line R2358D is provided. The phrase "genetic complement" is used to refer to the aggregate of nucleotide sequences, the expression of which sequences defines the phenotype of, in the present case, a *Catharanthus* plant, or a cell or tissue of that plant. A genetic complement thus represents the genetic makeup of a cell, tissue or plant, and a hybrid genetic complement represents the genetic makeup of a hybrid cell, tissue or plant. The invention thus provides *Catharanthus* plant cells that have a genetic complement in accordance with the *Catharanthus* plant cells disclosed herein, and plants, seeds and plants containing such cells. Plant genetic complements may be assessed by genetic marker profiles, and by the expression of phenotypic traits that are characteristic of the expression of the genetic complement, e.g., isozyme typing profiles. It is understood that *Catharanthus* hybrid 'PAS1305707' or *Catharanthus* line R2358D could be identified by any of the many well-known techniques such as, for example, Simple Sequence Length Polymorphisms (SSLPs) (Williams et al., Nucleic Acids Res., 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

In still yet another aspect, the present invention provides hybrid genetic complements, as represented by *Catharanthus* plant cells, tissues, plants, and seeds, formed by the combination of a haploid genetic complement of a *Catharanthus* plant of the invention with a haploid genetic complement of a second *Catharanthus* plant, preferably, another, distinct *Catharanthus* plant. In another aspect, the present invention provides a *Catharanthus* plant regenerated from a tissue culture that comprises a hybrid genetic complement of this invention.

In still yet another aspect, the invention provides a method of determining the genotype of a plant of *Catharanthus* hybrid 'PAS1305707' or *Catharanthus* line R2358D comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In one aspect, the invention provides a method of producing a *Catharanthus* seed, the method comprising (a) obtaining a plant of the present invention, wherein the plant has been cultivated to maturity; and (b) collecting a *Catharanthus* seed from the plant.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

Any embodiment discussed herein with respect to one aspect of the invention applies to other aspects of the invention as well, unless specifically noted.

DETAILED DESCRIPTION OF THE INVENTION

The invention provides methods and compositions relating to plants, seeds, and derivatives of *Catharanthus* hybrid 'PAS1305707' and *Catharanthus* line R2358D.

The hybrid 'PAS1305707' was produced by the cross of parent lines R2358D and M6948D. The parent lines show uniformity and stability within the limits of environmental influence. By crossing the parent lines, uniform plants of hybrid 'PAS1305707' can be obtained.

A. Origin and Breeding History of *Catharanthus* Hybrid 'PAS1305707'

The parents of hybrid 'PAS1305707' are R2358D and M6948D with R2358D used as the female parent. These parents were created as follows:

*Catharanthus* hybrid 'PAS1305707' originated from a cross in 2014 between two proprietary inbred lines. The cross was made between parental lines R2358D×M6948D in a greenhouse in Guadalupe, Calif. In 2014 the hybrid was trialed in California and Florida. In both locations the hybrid was evaluated for general horticultural characters. At a research station located near Ruskin, Fla. the hybrid was evaluated for general horticultural characters and field resistance to disease.

The hybrid cross was repeated in 2015, and seed was sent to research stations in California, Illinois, and Florida for repeat evaluation. The habit, color, and other horticultural characters were uniform and stable.

In 2015, a large production test was conducted in Guatemala to evaluate seed yield and seed quality of the hybrid. Seed from this production test was sent to research stations in California, Illinois, and Texas for evaluation in 2016. The hybrid was designated 'PAS1305707' and has shown uniformity and stability, as described in the cultivar description information.

B. Origin and Breeding History of *Catharanthus* Female Inbred Line R2358D

The inbred line R2358D was developed using the pedigree breeding system. The original developmental cross was made in the greenhouses in Guadalupe, Calif. in 2009 using two proprietary inbred lines 09-0592×09-0949.

The resulting $F_1$ from this cross was sown in a greenhouse in 2010 and bulk-sibbed to produce $F_2$ seed. In 2011, the $F_2$ population was evaluated, and single plant selections were made for general horticultural characters, including a well branched habit, large flowers, and disease resistance.

Several $F_3$ families were selected in 2012 that were the most uniform for the above characters. Single plant selections were made to produce $F_4$ families. Under Florida growing conditions, $F_3$ families were also evaluated for horticultural characters and field resistance to disease.

Subsequent $F_4$ to $F_5$ generations were advanced from 2012 through 2014 using self-pollinated single plant selections, while continuing to select families with the most uniform previously described characters. One of the $F_5$ families was massed in 2014 to produce breeder's seed. In 2015, the massed seed from 2014 was used to make stock seed.

The plants massed in 2014 and 2015 were uniform and stable. No variants or off-types were observed in either the breeder's seed increase or the stock seed increase.

The inbred line was designated R2358D. It was stable and uniform after two generations of seed increase, which included the breeder's seed increase and the stock seed increase.

C. Origin and Breeding History of *Catharanthus* Male Inbred Line M6948D

The inbred line M6948D was developed using the pedigree breeding system. The original germplasm dates back to 2003 from a proprietary inbred developed from earlier *vinca* breeding. The $F_6$ inbred was designated 03-070 and was developed in the greenhouses in Guadalupe, Calif.

In 2008, the $F_6$ inbred line 03-070 was sown in the Guadalupe greenhouses and was evaluated under Florida growing condition for horticultural characters and field resistance to disease. Single plant selections were made in the greenhouse and advanced to the $F_7$ generation.

In 2009, single plant selections were again evaluated and single plants selections were made and self-pollinated to produce $F_8$ families.

One of the $F_8$ families was massed in 2010 to produce breeder's seed. In 2011, the massed seed from 2010 was used to make stock seed.

The plants massed in 2010 and the plants massed in 2011 were uniform and stable. No variants or off-types were observed in either the breeder's seed increase or the stock seed increase.

The inbred line was designated M6948D. It was stable and uniform after two generations of seed increase, which included the breeder's seed increase and the stock seed increase.

D. Physiological and Morphological Characteristics of *Catharanthus* Hybrid 'PAS1305707' and *Catharanthus* Line R2358D The new hybrid cultivar 'PAS1305707' and female inbred line R2358D have not been observed under all possible environmental conditions to date. As is known in the art, it is possible that the phenotypes may vary somewhat with variations in the environment, such as temperature, light intensity, and day length, without, however, any variance in genotype.

The following descriptions and measurements describe plants produced from seed and grown in a glass-covered greenhouse under conditions comparable to those used in commercial practice. The plants were grown utilizing a soilless growth medium in one-gallon containers for 21 weeks in Guadalupe, Calif. Greenhouse temperatures were maintained at approximately 75° F. to 85° F. (24° C. to 30° C.) during the day and approximately 65° F. to 68° F. (18° C. to 20° C.) during the night. No supplemental lighting was provided.

The chart used in the identification of colors described herein is the Pantone Plus Series Color Bridge, 2nd Edition, except where general color terms of ordinary significance are used. The color values were determined in February 2020 under natural light conditions in Guadalupe, Calif. Measurements and numerical values represent averages of typical plants.

A description of the physiological and morphological characteristics of the plants described herein are presented in the tables that follow.

TABLE 1

Physiological and Morphological Characteristics of Hybrid 'PAS1305707'

| CHARACTERISTIC | 'PAS1305707' | 'PAS1053045' |
|---|---|---|
| 1. OVERALL PLANT HABIT (at flowering stage): | | |
| Species: 1 = *C. roseus*; 2 = Other | 1 | 1 |
| Ploidy: 1 = Haploid; 2 = Diploid; 3 = Triploid; 4 = Tetrapioid | 2 | 2 |
| Life Cycle: 1 = Annual; 2 = Biennial; 3 = Perennial | 1 | 1 |

TABLE 1-continued

Physiological and Morphological Characteristics of Hybrid 'PAS1305707'

| CHARACTERISTIC | 'PAS1305707' | 'PAS1053045' |
|---|---|---|
| Growth Habit: 1 = Determinate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 56 | 68 |
| Length of Flowering Season in Days | Until frost | Until frost |
| Plant Height at Maturity (cm) | 23.7 | 28.6 |
| Plant Width at Maturity (cm) | 29.4 | 40.1 |
| Plant Height Class: 1 = Extra Dwarf; 2 = Dwarf; 3 = Semi-dwarf; 4 = Tall | 3 | 3 |
| Plant Width Class: 1 = Compact; 2 = Semi-compact; 3 = Spreading/Lax | 2 | 2 |
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 24.6 | 28.1 |
| Number of Internodes Below First Branch | 1 | 1 |
| Number of First Order Branches (From Main Stem) | 14 | 13 |
| Stem Anthocyanin: 1 = Absent; 2 = Along Veins Only; 3 = Solid Coloration | 1 | 1 |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 1 | 1 |
| Petiole Anthocyanin: 1 = Absent; 2 = Mild; 3 = Strong | 1 | 1 |
| Leaf Shape: 1 = Lanceolate; 2 = Elliptic; 3 = Obovate; 4 = Ovate | 2 | 2 |
| Leaf Width (mm) | 34.2 | 29.1 |
| Leaf Length (mm) | 87.1 | 106.2 |
| LEAF DORSAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 2 | 2 |
| Color Chart Code | 371C | 371C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 1 | 1 |
| Pedicel Anthocyanin: 1 = Absent; 2 = Faint; 3 = Strong | 1 | 1 |
| Number Flowers per Plant | 18 | 25 |
| Flower Diameter (mm) | 59 | 64 |
| Orifice Size Including the Opening of the Corolla Tube (mm) | 3 | 3 |
| Petal Width At Widest Point (mm) | 38 | 37 |
| Petal Length From Outside Orifice to Outer Edge (mm) | 29 | 32 |
| 5. FLOWER COLORS: | | |
| Petal Color Chart Code | 2415C | 2060C |
| Orifice Color Chart Code | 2425C | 2063C |
| 6. SEEDS (Mature (Dry) Seeds): | | |
| Seed Set: 1 = None; 2 = Poor; 3 = Fair; 4 = Good; 5 = Excellent | 4 | 4 |
| Seed Coat Color: 1 = White; 2 = Tan; 3 = Brown; 4 = Black; 5 = Other | 4 | 4 |
| Seed Weight (mg/1000 Seeds) | 1,641 | 1,944 |

*These are typical values. Values may vary due to environment. Other values that are substantially equivalent are also within the scope of the invention.

TABLE 2

Physiological and Morphological Characteristics of Line R2358D and 'PAS1305707'

| CHARACTERISTIC | R2358D | 'PAS1305707' |
|---|---|---|
| 1. OVERALL PLANT HABIT (at flowering stage): | | |
| Species: 1 = *C. roseus*; 2 = Other | 1 | 1 |
| Ploidy: 1 = Haploid; 2 = Diploid; 3 = Triploid; 4 = Tetrapioid | 2 | 2 |
| Life Cycle: 1 = Annual; 2 = Biennial; 3 = Perennial | 1 | 1 |
| Growth Habit: 1 = Determinate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 63 | 56 |
| Length of Flowering Season in Days | Until frost | Until frost |
| Plant Height at Maturity (cm) | 18.8 | 23.7 |
| Plant Width at Maturity (cm) | 27.7 | 29.4 |
| Plant Height Class: 1 = Extra Dwarf; 2 = Dwarf; 3 = Semi-dwarf; 4 = Tall | 2 | 3 |
| Plant Width Class: 1 = Compact; 2 = Semi-compact; 3 = Spreading/Lax | 1 | 2 |
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 19.8 | 24.6 |
| Number of Internodes Below First Branch | 1 | 1 |
| Number of First Order Branches (From Main Stem) | 12 | 14 |
| Stem Anthocyanin: 1 = Absent; 2 = Along Veins Only; 3 = Solid Coloration | 2 | 1 |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 1 | 1 |
| Petiole Anthocyanin: 1 = Absent; 2 = Mild; 3 = Strong | 1 | 1 |
| Leaf Shape: 1 = Lanceolate; 2 = Elliptic; 3 = Obovate; 4 = Ovate | 2 | 2 |
| Leaf Width (mm) | 35.7 | 34.2 |
| Leaf Length (mm) | 76.6 | 87.1 |
| LEAF DORSAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 2 | 2 |
| Color Chart Code | 371C | 371C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 1 | 1 |
| Pedicel Anthocyanin: 1 = Absent; 2 = Faint; 3 = Strong | 1 | 1 |
| Number Flowers per Plant | 15 | 18 |
| Flower Diameter (mm) | 60 | 59 |
| Orifice Size Including the Opening of the Corolla Tube (mm) | 3 | 3 |
| Petal Width At Widest Point (mm) | 38 | 38 |
| Petal Length From Outside Orifice to Outer Edge (mm) | 29 | 29 |
| 5. FLOWER COLORS: | | |
| Petal Color Chart Code | 2063C | 2415C |
| Orifice Color Chart Code | 2425C | 2425C |

TABLE 2-continued

Physiological and Morphological Characteristics of Line R2358D and 'PAS1305707'

| CHARACTERISTIC | R2358D | 'PAS1305707' |
|---|---|---|
| 6. SEEDS (Mature (Dry) Seeds): | | |
| Seed Set: 1 = None; 2 = Poor; 3 = Fair; 4 = Good; 5 = Excellent | 4 | 4 |
| Seed Coat Color: 1 = White; 2 = Tan; 3 = Brown; 4 = Black; 5 = Other | 4 | 4 |
| Seed Weight (mg/1000 Seeds) | 1,408 | 1,641 |

*These are typical values. Values may vary due to environment. Other values that are substantially equivalent are also within the scope of the invention.

E. Distinguishing Characteristics of Hybrid 'PAS1305707' and Parent Inbred Line R2358D The closest commercial comparison for 'PAS1305707' of the present invention is believed to be 'PAS1053045', marketed as Valiant Lilac. In addition, 'PAS1305707' can be distinguished from its female parent, inbred line R2358D. Distinguishing characteristics were evaluated in both a greenhouse trial grown in Guadalupe, Calif., and two field trials grown in Elburn, Ill.

For the Guadalupe, Calif. trial, plants were produced from seed and grown in a glass-covered greenhouse under conditions comparable to those used in commercial practice. The plants were grown utilizing a soilless growth medium in one-gallon containers for 21 weeks. Greenhouse temperatures were maintained at approximately 75° F. to 85° F. (24° C. to 30° C.) during the day and approximately 65° F. to 68° F. (18° C. to 20° C.) during the night. No supplemental lighting was provided.

In comparison, the plants from the Elburn, Ill. trials were produced from seed and grown in a glass-covered greenhouse under conditions comparable to those used in commercial practice using trays having deep 2⅜"×2⅜" growing cells and a soilless growth medium. Plants were transplanted to the field in early summer. Data was collected after 15 weeks of outdoor growth for Trial 1, and after 12 weeks for Trial 2.

Table 3 illustrates that plants of 'PAS1305707' are significantly shorter than plants of 'PAS1053045'. In addition, Table 4 and Table 5 show that 'PAS1305707' has significantly shorter and wider leaves than plants of 'PAS1053045'. Table 1 illustrates that flower petals of 'PAS1305707' are a different color when compared to 'PAS1053045'. This trait is consistent across all trials conducted.

As shown in Table 6, 'PAS1305707' has significantly longer leaves than inbred line R2358D.

TABLE 3

Plant height differences between Hybrids 'PAS1305707' and 'PAS1053045'

| Trial | 'PAS1305707' Avg. Plant Height (cm) | 'PAS1053045' Avg. Plant Height (cm) | Sample Size Each Variety | t Critical $\alpha = .05$ | t Statistic | P Value |
|---|---|---|---|---|---|---|
| Elburn 1 | 41.0 +/− 3.1 | 45.9 +/− 2.2 | 10 | 2.1 | 4.1 | 6.8E−04 |
| Guadalupe | 23.7 +/− 1.8 | 28.6 +/− 1.5 | 10 | 2.1 | 6.5 | 3.7E−06 |

TABLE 4

Leaf length differences between Hybrids 'PAS1305707' and 'PAS1053045'

| Trial | 'PAS1305707' Avg. Leaf Length (mm) | 'PAS1053045' Avg. Leaf Length (mm) | Sample Size Each Variety | t Critical $\alpha = .05$ | t Statistic | P Value |
|---|---|---|---|---|---|---|
| Elburn 1 | 61.6 +/− 5.8 | 77.6 +/− 7.7 | 25 | 2.0 | 8.3 | 6.9E−11 |
| Guadalupe | 87.1 +/− 3.3 | 106.2 +/− 3.5 | 10 | 2.1 | 12.6 | 2.3E−10 |

TABLE 5

Leaf width differences between Hybrids 'PAS1305707' and 'PAS1053045'

| Trial | 'PAS1305707' Avg. Leaf Width (mm) | 'PAS1053045' Avg. Leaf Width (mm) | Sample Size Each Variety | t Critical $\alpha = .05$ | t Statistic | P Value |
|---|---|---|---|---|---|---|
| Elburn 1 | 28.5 +/− 2.3 | 24.4 +/− 3.0 | 25 | 2.0 | −5.4 | 2.0E−06 |
| Guadalupe | 34.2 +/− 1.4 | 29.1 +/− 1.5 | 10 | 2.1 | −7.8 | 3.5E−07 |

TABLE 6

Leaf length differences between Hybrid 'PAS1305707' and R2358D

| Trial | 'PAS1305707' Avg. Leaf Length (mm) | R2358D Avg. Leaf Length (mm) | Sample Size Each Variety | t Critical α = .05 | t Statistic | P Value |
|---|---|---|---|---|---|---|
| Elburn 2 | 72.6 +/− 4.7 | 61.0 +/− 4.5 | 10 | 2.1 | 5.7 | 2.3E−05 |
| Guadalupe | 87.1 +/− 3.3 | 76.6 +/− 3.7 | 10 | 2.1 | 6.7 | 2.6E−06 |

F. Breeding *Catharanthus* Plants

One aspect of the current invention concerns methods for producing seed of *Catharanthus* hybrid 'PAS1305707' involving crossing *Catharanthus* lines R2358D and M6948D. Alternatively, in other embodiments of the invention, hybrid 'PAS1305707' or line R2358D may be crossed with itself or with any second plant. Such methods can be used for propagation of hybrid 'PAS1305707' or the *Catharanthus* line R23581D, or can be used to produce plants that are derived from hybrid 'PAS1305707' or *Catharanthus* line R2358D. Plants derived from *Catharanthus* hybrid 'PAS1305707' or *Catharanthus* line R2358D may be used, in certain embodiments, for the development of new *Catharanthus* varieties.

The development of new varieties using one or more starting varieties is well known in the art. In accordance with the invention, novel varieties may be created by crossing hybrid 'PAS1305707' followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can be used to improve a variety, and may be used, for example, to introduce a desired allele or trait into the plant genetic background of any plant that is sexually compatible with a plant of the present invention. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, the progeny have the characteristic being transferred, but are like the superior parent for most or almost all other loci. The last backcross generation would be selfed to give pure breeding progeny for the trait being transferred.

G. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those *Catharanthus* plants which are developed by a plant breeding technique called backcrossing or by genetic engineering, wherein essentially all of the morphological and physiological characteristics of a variety are recovered or conserved in addition to the single locus introduced into the variety via the backcrossing or genetic engineering technique, respectively. By essentially all of the morphological and physiological characteristics, it is meant that the characteristics of a plant are recovered or conserved that are otherwise present when compared in the same environment, other than an occasional variant trait that might arise during backcrossing, introduction of a transgene, or application of a genetic engineering technique.

Backcrossing methods can be used with the present invention to improve or introduce a characteristic into the present variety. The parental *Catharanthus* plant which contributes the locus for the desired characteristic is termed the nonrecurrent or donor parent. This terminology refers to the fact that the nonrecurrent parent is used one time in the backcross protocol and therefore does not recur. The parental *Catharanthus* plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a plant is obtained wherein essentially all of the morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The selection of a suitable recurrent parent therefore is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of desired genetic, and therefore the desired physiological and morphological constitution of the original variety. The choice of the particular nonrecurrent parent will depend on the purpose of the backcross, one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

In one embodiment, progeny *Catharanthus* plants of a backcross in which a plant described herein is the recurrent parent comprise (i) the desired trait from the non-recurrent parent and (ii) all of the physiological and morphological characteristics of the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

The plants of the present invention are particularly well suited for the development of new lines based on the genetic background of the plants. In selecting a second plant to cross with *Catharanthus* hybrid 'PAS1305707' or *Catharanthus* line R2358D for the purpose of developing novel *Catharanthus* lines, it will typically be preferred to choose those plants which either themselves exhibit one or more selected desirable characteristics or which exhibit the desired characteristic(s) when in hybrid combination. Examples of desirable traits may include, in specific embodiments, high flower yield, flower quality, high seed germination, seedling vigor, disease resistance, and adaptability for soil and climate conditions such as drought or heat. Consumer-driven traits, such as flower color, shape, and texture are other examples of traits that may be incorporated into new lines of *Catharanthus* plants developed by this invention.

In other embodiments, the invention provides methods of vegetatively propagating a *Catharanthus* plant of the present invention. Such a method may comprise the steps of: (a) collecting tissue capable of being propagated from said plant; and (b) propagating a *Catharanthus* plant from said tissue.

In still further embodiments, a plant of the invention is propagated by seed, wherein a plant may be used as either a female or a male parent for producing progeny seed and plants.

Also provided are methods of producing a *Catharanthus* plant of the present invention, said method comprising introgressing a desired allele from a plant comprising the allele into a plant of a different genotype. In certain embodiments, such an allele may be inherited from or introgressed into *Catharanthus* hybrid 'PAS1305707' or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of *Catharanthus* plants for breeding is not necessarily dependent on the phenotype of a plant and instead can be based on genetic investigations. Thus, in one embodiment, the invention provides the genetic complement of a *Catharanthus* plant as described herein. "Genetic complement" as used herein refers to the aggregate of nucleotide sequences, the expression of which sequences defines the phenotype of, in the present case, a *Catharanthus* plant, or a cell or tissue of that plant. A genetic complement thus represents the genetic makeup of a cell, tissue or plant, and a hybrid genetic complement represents the genetic makeup of a hybrid cell, tissue or plant. The genetic complement of variety 'PAS1305707' may be identified by any of the many well-known techniques in the art. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection.

Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accordance with the invention include, but are not necessarily limited to, Simple Sequence Length Polymorphisms (SSLPs) (Williams et al., *Nucleic Acids Res.,* 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into a line. This molecular breeding-facilitated movement of a trait or traits into a line or variety may encompass incorporation of a particular genomic fragment associated with a particular trait of interest into the line or variety by the mechanism of identification of the integrated genomic fragment with the use of flanking or associated marker assays. In the embodiment represented here, one, two, three or four genomic loci, for example, may be integrated into a line via this methodology. When this line containing the additional loci is further crossed with another parental line to produce hybrid offspring, it is possible to then incorporate at least eight separate additional loci into the hybrid. These additional loci may confer, for example, such traits as disease resistance, drought or heat tolerance, or a flower quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

In particular embodiments of the invention, marker assisted selection is used to increase the efficiency of a backcrossing breeding scheme for producing a *Catharanthus* line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

H. Plants Derived by Genetic Engineering

Various genetic engineering technologies have been developed and may be used by those of skill in the art to introduce traits in plants. In certain aspects of the claimed invention, traits are introduced into *Catharanthus* plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved *Catharanthus* lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a *Catharanthus* plant genome (see, for example Sauer et al., *Plant Physiol*, 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment, genetic transformation may be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Nat. Biotechnol., 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107: 462-469, 2003).

A number of promoters have utility for plant gene expression for any gene of interest including but not limited to selectable markers, scoreable markers, genes for pest tolerance, disease resistance, or any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., Nature, 313:810, 1985), including in monocots (see, e.g., Dekeyser et al., Plant Cell, 2:591, 1990; Terada and Shimamoto, Mol. Gen. Genet., 220:389, 1990); a tandemly duplicated version of the CaMV 35S promoter, the enhanced 35S promoter (P-e35S); 1 the nopaline synthase promoter (An et al., Plant Physiol., 88:547, 1988); the octopine synthase promoter (Fromm et al., Plant Cell, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., EMBO J., 4:2723, 1985), (3) hormones, such as abscisic acid (Marcotte et al., *Plant Cell*, 1:969, 1989), (4) wounding (e.g., wunI, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a *Catharanthus* plant according to the invention. Non-limiting examples of particular genes and corresponding phenotypes one may choose to introduce into a *Catharanthus* plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird *Biotech. Gen. Engin. Rev.*, 9:207, et al., 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

I. Definitions

In the description and tables herein, a number of terms are used. In order to provide a clear and consistent understanding of the specification and claims, the following definitions are provided:

Allele: Any of one or more alternative forms of a genetic locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid (F1), back to one of the parents of the hybrid progeny. Backcrossing can be used to introduce one or more single locus conversions or transgenes from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Plant Part: As used herein, a plant part refers to a part of a plant of the present invention. A plant part may be defined as comprising a cell of such plant, such as a cutting, a leaf, an ovule, pollen, a cell, a seed, a flower, an embryo, a meristem, a cotyledon, an anther, a root, a root tip, a pistil, a stem, and a protoplast or callus derived therefrom.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing or genetic engineering of a locus, wherein essentially all of the morphological and physiological characteristics of a *Catharanthus* variety are recovered in addition to the characteristics of the single locus transferred into the variety via the backcrossing technique or genetic engineering technique.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a *Catharanthus* plant by transformation.

*Catharanthus* plant: As used herein, *Catharanthus* refers to any plant from the genus *Catharanthus*, which may include but is not limited to *Catharanthus* pusillus, *Catharanthus* roseus, *Catharanthus* longifolius, *Catharanthus* ovalis, *Catharanthus* trichophyllus, and the like.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

J. Deposit Information

A deposit of *Catharanthus* hybrid 'PAS1305707' and parent line R2358D, disclosed above and recited in the claims, has been made with the Provasoli-Guillard National Center for Marine Algae and Microbiota (NCMA), 60 Bigelow Drive, East Boothbay, Maine, 04544 USA. Each deposit was made on Jul. 22, 2022. The accession numbers for those deposited seeds of *Catharanthus* hybrid 'PAS1305707' and inbred parent line R2358D are NCMA Accession Number 202207074, and NCMA Accession Number 202207071, respectively. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A *Catharanthus* plant comprising at least a first set of the chromosomes of *Catharanthus* line R2358D, a sample of seed of said line having been deposited under NCMA Accession Number 202207071.

2. A *Catharanthus* seed that produces the plant of claim 1.

3. Plant of claim 1, wherein the plant is a plant of said *Catharanthus* line R2358D.

4. The plant of claim 1, wherein said plant is a hybrid *Catharanthus* plant.

5. The seed of claim 2, wherein the seed is a seed of said *Catharanthus* line R2358D.

6. The seed of claim 2, wherein the seed is a seed of a hybrid *Catharanthus* plant.

7. The plant of claim 4, wherein the hybrid plant is a plant of *Catharanthus* hybrid 'PAS1305707', a sample of seed of said hybrid 'PAS1305707' having been deposited under NCMA Accession Number 202207074.

8. The seed of claim 6, wherein the seed is a seed of *Catharanthus* hybrid 'PAS1305707', a sample of seed of said hybrid 'PAS1305707' having been deposited under NCMA Accession Number 202207074.

9. A plant part of the plant of claim 1.

10. The plant part of claim 9, further defined as a flower, pollen, a leaf, an ovule, an embryo, a seed, or a cell.

11. A *Catharanthus* plant having all of the physiological and morphological characteristics of the plant of claim 7.

12. A tissue culture of regenerable cells of the plant of claim 1.

13. A *Catharanthus* plant regenerated from the tissue culture of claim 12.

14. A method of vegetatively propagating a *Catharanthus* plant, the method comprising the steps of:
(a) collecting tissue capable of being propagated from the plant of claim 1; and
(b) propagating a *Catharanthus* plant from said tissue.

15. A method of introducing a trait into a *Catharanthus* line, the method comprising:
(a) utilizing as a recurrent parent the plant of claim 1 by crossing said plant with a donor plant that comprises a trait to produce $F_1$ progeny;
(b) selecting an $F_1$ progeny that comprises the trait;
(c) backcrossing the selected $F_1$ progeny with the same line used as the recurrent parent in step (a) to produce backcross progeny;
(d) selecting a backcross progeny that comprises the trait and otherwise comprises the physiological and morphological characteristics of the recurrent parent line used in step (a); and
(e) repeating steps (c) and (d) three or more times to produce a selected fourth or higher backcross progeny.

16. A *Catharanthus* plant produced by the method of claim 15.

17. A method of producing a plant comprising an added trait, the method comprising introducing a transgene conferring the trait into the plant of claim 1.

18. A *Catharanthus* plant produced by the method of claim 17.

19. A *Catharanthus* plant comprising at least a first set of the chromosomes of *Catharanthus* line R2358D, a sample of seed of said line having been deposited under NCMA Accession Number 202207071, further comprising a transgene.

20. The plant of claim 19, wherein the transgene confers a trait selected from the group consisting of male sterility, herbicide tolerance, insect resistance, pest resistance, disease resistance, and environmental stress tolerance.

21. A *Catharanthus* plant comprising at least a first set of the chromosomes of *Catharanthus* line R2358D, a sample of seed of said line having been deposited under NCMA Accession Number 202207071, further comprising a single locus conversion.

22. The plant of claim 21, wherein the single locus conversion confers a trait selected from the group consisting of male sterility, herbicide tolerance, insect resistance, pest resistance, disease resistance, and environmental stress tolerance.

23. A method for producing a seed of a plant derived from at least one of hybrid 'PAS1305707' or line R2358D, the method comprising the steps of:
(a) crossing the plant of claim 1 with itself or a second *Catharanthus* plant; and
(b) allowing seed of a hybrid 'PAS1305707'- or line R2358D-derived *Catharanthus* plant to form.

24. A method for producing a seed of a hybrid 'PAS1305707'- or line R2358D-derived *Catharanthus* plant, the method comprising the steps of
(a) producing a hybrid 'PAS1305707'- or line R2358D-derived *Catharanthus* plant from a seed produced by crossing the plant of claim 1 with itself or a different *Catharanthus* plant; and
(b) crossing the hybrid 'PAS1305707'- or line R2358D-derived *Catharanthus* plant with itself or a different *Catharanthus* plant to obtain seed of a further hybrid 'PAS1305707'- or line R2358D-derived *Catharanthus* plant.

25. The method of claim 24, the method further comprising repeating said producing and crossing steps of (a) and (b) using the seed from said step (b) for producing the plant according to step (a) for at least one generation to produce a seed of an additional hybrid 'PAS1305707'- or line R2358D-derived *Catharanthus* plant.

26. A plant part of the plant of claim 7.

27. The plant part of claim 26, further defined as a flower, pollen, a leaf, an ovule, a seed, or a cell.

28. A method of producing a *Catharanthus* seed, the method comprising:
(a) obtaining the plant of claim 1, wherein the plant has been cultivated to maturity; and
(b) collecting a *Catharanthus* seed from the plant.

* * * * *